United States Patent [19]

Strecker et al.

[11] Patent Number: 5,856,538

[45] Date of Patent: Jan. 5, 1999

[54] PREPARATION OF N-ACYLAMINO CARBOXYLIC ACIDS AND N-ACYLAMINO SULFONIC ACIDS AND THEIR ALKALI METAL SALTS

[75] Inventors: Beate Strecker, Ludwigshafen; Alfred Oftring, Bad Dürkheim; Dieter Hertel, Leimen; Georg Schuh, Ludwigshafen, all of Germany

[73] Assignee: BASF Aktiengesellschaft, Ludwigshafen, Germany

[21] Appl. No.: 809,139

[22] PCT Filed: Sep. 12, 1995

[86] PCT No.: PCT/EP95/03584

§ 371 Date: Mar. 24, 1997

§ 102(e) Date: Mar. 24, 1997

[87] PCT Pub. No.: WO96/09278

PCT Pub. Date: Mar. 28, 1996

[30]   Foreign Application Priority Data

Sep. 23, 1994 [DE] Germany ............... 44 33 977.1

[51] Int. Cl.$^6$ ............. C07C 231/00; C07C 205/00; C07C 229/00
[52] U.S. Cl. ............. 554/63; 554/49; 562/553; 562/574; 562/575; 562/105
[58] Field of Search ............ 554/63, 49; 562/553, 562/574, 575, 105

[56]   References Cited

U.S. PATENT DOCUMENTS

| | | | |
|---|---|---|---|
| 1,932,180 | 10/1933 | Guenther et al. | 260/124 |
| 3,836,551 | 9/1974 | Schroeder et al. | 260/404 |
| 4,233,229 | 11/1980 | Chakrabarti | 260/401 |

FOREIGN PATENT DOCUMENTS

WO 95/07881  3/1995  WIPO.

*Primary Examiner*—Gary Geist
*Assistant Examiner*—Brian J. Davis
*Attorney, Agent, or Firm*—Oblon, Spivak, McClelland, Maier & Neustadt, P.C.

[57]   ABSTRACT

N-acylamino carboxylic acids and N-acylamino sulfonic acids and their alkali metal salts from the technical alkali metal salts of amino carboxylic acids and amino sulfonic acids, respectively, with an active content of 50–95% by weight, based on the solids content of the technical alkali metal salts, and from alkyl carboxylates, are prepared by (a) preparing a suspension of the solid anhydrous technical alkali metal salts of the amino carboxylic acids or amino sulfonic acids in the alkyl carboxylates, (b) reacting this suspension by adding more than 30 to 150 mol % of strong bases to give the alkali metal salts of the N-acylamino carboxylic acids or N-acylamino sulfonic acids, and (c) if required preparing therefrom the free N-acylamino carboxylic acids or N-acylamino sulfonic acids in a conventional way by adding acids.

8 Claims, No Drawings

PREPARATION OF N-ACYLAMINO CARBOXYLIC ACIDS AND N-ACYLAMINO SULFONIC ACIDS AND THEIR ALKALI METAL SALTS

BACKGROUND OF THE INVENTION

1. Field of the Invention

The present invention relates to an improved process for preparing N-acylamino carboxylic acids and N-acylamino sulfonic acids and their alkali metal salts from the technical alkali metal salts of amino carboxylic acids and amino sulfonic acids, respectively, and from alkyl carboxylates.

2. Discussion of the Background

DE-A 20 04 099 discloses that salts of N-acylamino carboxylic acids can be prepared by acylation of the corresponding amino carboxylic acids or their salts with a carboxylic acid, a carboxylic ester or a carboxamide in the presence of an equivalent amount of a basic compound which forms salts with carboxylic acids, such as an alkali metal or alkaline earth metal hydroxide, at from 100° to 250° C., preferably from 160° to 200° C. In this case the basic compound merely serves to neutralize the amino carboxylic acids or carboxylic acids used. The reaction is carried out in the melt of amino carboxylic acid and acylating agent or in a suspension of the amino carboxylic acid in a solution of an acylating agent and of a basic organic nitrogen compound, eg. an amine, in a high-boiling organic solvent.

However, the disadvantages of the described reaction procedure are the long reaction times and the low yields, which are attributable essentially to the partial decomposition of the starting compounds and of the products because of the high reaction temperatures. This is because the reaction mixture becomes slightly dark in color during this and a slight evolution of carbon dioxide which is almost always observed can likewise be explained only by decomposition reactions.

German Patent Application P 44 08 957.0 describes a process for preparing N-acylamino carboxylic and sulfonic acids from the alkali metal salts of the underlying amino carboxylic and sulfonic acids, respectively, and alkyl carboxylates, in which 0.5 to 30 mol % of strong bases are added as catalyst to a suspension of the amino carboxylic and sulfonic acid salts, respectively, in the carboxylates. However, this process gives satisfactory results only on use of pure alkali metal amino carboxylates or sulfonates with an active content of more than 95% by weight, based on the solids content of the alkali metal salts. Use of corresponding salts of technical quality results in drastic losses of selectivity of up to 15%.

SUMMARY OF THE INVENTION

It is an object of the present invention to provide an efficient and economic preparation process which starts from technical alkali metal amino carboxylates or sulfonates and which gives good space-time yields of N-acylamino carboxylic acids and N-acylamino sulfonic acids or their alkali metal salts in high purities and selectivities.

We have found that this object is achieved by a process for preparing N-acylamino carboxylic acids and N-acylamino sulfonic acids and their alkali metal salts from the technical alkali metal salts of amino carboxylic acids and amino sulfonic acids, respectively, with an active content of 50–95% by weight, preferably 70–94% by weight, in particular 80–93% by weight, based on the solids content of the technical alkali metal salts, and from alkyl carboxylates, which comprises (a) preparing a suspension of the solid anhydrous technical alkali metal salts of the amino carboxylic acids or amino sulfonic acids in the alkyl carboxylates, (b) reacting this suspension by adding 30 to 150 mol % of strong bases over the amount required for neutralization to give the alkali metal salts of the N-acylamino carboxylic acids or N-acylamino sulfonic acids, and (c) if required preparing therefrom the free N-acylamino carboxylic acids or N-acylamino sulfonic acids in a conventional way by adding acids.

DETAILED DESCRIPTION OF THE PREFERRED EMBODIMENTS

The procedure in step (a) is, for example, for the alkyl carboxylates and the solid anhydrous technical alkali metal salts of the amino carboxylic acids or amino sulfonic acids to be introduced into a suitable vessel of glass or another material and processed with a conventional suspending agitator to give a fine-particle suspension.

However, the suspension can also be prepared in step (a) by mixing together the alkyl carboxylates and an aqueous solution of the technical alkali metal salts of the amino carboxylic acids or amino sulfonic acids in a suitable vessel of glass or another material, and subsequently removing the water from the mixture as quickly as possible by heating and applying a vacuum. It is possible to observe, surprisingly, that during this there is only very slight (usually less than 2%) hydrolysis of the alkyl carboxylates to the alkali metal salts of the underlying carboxylic acids. The advantage of using such aqueous solutions is that it is possible to use aqueous solutions, produced in the industrial synthetic process, of impure alkali metal salts of amino carboxylic acids or amino sulfonic acids without further processing such as spray drying. In addition, the problems associated with the handling of solids do not arise, such as dust formation or uniform metering in.

Technical alkali metal salts of amino carboxylic acids contain a range of subsidiary components; in the case of, for example, technical sarcosine sodium, which is usually prepared by the Strekker reaction of methylamine with formaldehyde and hydrocyanic acid and subsequent hydrolysis of the methylaminoacetonitrile formed, these are mainly other amino carboxylates, eg. methyliminodiacetate or dimethylglycinate, carboxylates such as alkali metal salts of glycolic acid, and formate.

As a rule, the suspension in step (a) is prepared from equimolar or approximately equimolar amounts of technical alkali metal salts of amino carboxylic acids or amino sulfonic acids and alkyl carboxylates, an excess of up to 15 mol %, in particular up to 10 mol %, of one of the two components being defensible. A larger excess of alkyl carboxylate, for example as diluent, is normally unnecessary.

The strong bases are added in step (b) to the suspension prepared in step (a) in order to start the reaction. The bases are usually added after or during the heating of the suspension to the reaction temperature, but can also be added during the preparation of the suspension in step (a), for example together with the alkali metal salts of the amino carboxylic acids or amino sulfonic acids, or shortly before the heating of the suspension. The bases can be used as solid substances or in dissolved form, for example in an organic solvent such as an alcohol.

The amount of strong bases used is 30 to 150 mol %, preferably 70 to 135 mol %, in particular 80 to 125 mol %, especially 90 to 115 mol %, over the amount required for neutralization, based on the technical alkali metal salts of the amino carboxylic acids or amino sulfonic acids. It is possible to use a single species of a strong base or a mixture of various bases.

Particularly suitable strong bases are:

alcoholates, especially alkali metal alcoholates of $C_1$–$C_4$-alkanols, eg. sodium methanolate, sodium ethanolate, sodium isopropoxide or potassium tert-butoxide;

hydrides, eg. sodium hydride, sodium borohydride or lithium aluminum hydride;

alkali metal or alkaline earth metal hydroxides, eg. sodium hydroxide, potassium hydroxide, lithium hydroxide or calcium hydroxide;

alkali metal carbonates, eg. sodium carbonate, potassium carbonate or lithium carbonate;

amide salts, eg. lithium diisopropylamide;

organolithium compounds such as alkyllithium compounds, eg. n-butyllithium or methyllithium, or phenyllithium.

Of these, alcoholates are preferred.

The reaction in step (b) is carried out in a relatively mild temperature range, usually at 50° to 150° C., in particular at 80° to 140° C., especially at 100° to 130° C. The reaction is normally carried out under atmospheric pressure; although autogenous pressure or elevated pressure is possible, it has no further advantages.

Alkyl carboxylate is usually no longer detected by analytical methods, eg. infrared (IR) spectroscopy, in the reaction mixture 1 to 2 hours after addition of the base. The alkanols produced in the reaction from the alkyl carboxylates usually distil out of the reaction mixture, where appropriate under reduced pressure, or remain, at least in part, in the reaction mixture. After the reaction is complete, the reaction mixture is normally in the form of a viscous paste. This can be dissolved after the temperature has been lowered, for example to 80° to 100° C., by adding water. This results, for example, in approximately 30–40% by weight aqueous solutions of the alkali metal salts of the N-acylamino carboxylic acids or N-acylamino sulfonic acids.

If the intention is to obtain the free N-acylamino carboxylic acids or N-acylamino sulfonic acids, these are prepared in step (c) from the alkali metal salts in a conventional way by adding acids. Particularly suitable acids are mineral acids such as sulfuric acid, phosphoric acid or hydrochloric acid, which are usually added at room temperature to the aqueous solutions of the alkali metal salts of N-acylamino carboxylic acids or N-acylamino sulfonic acids, so that the pH is adjusted to the range from about 0 to 3, in particular 1 to 2. This normally results in milky creamy emulsions. These emulsions are advantageously separated using a conventional phase separation aid, eg. ketones such as isobutyl methyl ketone or methyl ethyl ketone, alkanols such as n-butanol, isobutanol or sec-butanol, ethers such as methyl tert-butyl ether or diisopropyl ether, $C_1$–$C_4$-alkyl acetates, $C_1$–$C_4$-alkyl propionates or acetoacetic esters, which can be added at the same time as the acids or after formation of the emulsion, at slightly elevated temperature, for example at 40° to 70° C. Phase separation aids of this type are normally low-boiling compounds which have little or no miscibility with water and can be used at reasonable cost on the industrial scale.

The process according to the invention can be applied particularly satisfactorily when the technical alkali metal salts of amino carboxylic acids used are the sodium or potassium salts of aliphatic amino carboxylic acids having 2 to 10 carbons, preferably 3 to 6 carbons, in particular of valine, leucine, norleucine, glycine, alanine, β-alanine, ε-aminocaproic acid, α-aminoisobutyric acid, sarcosine (N-methylglycine), aspartic acid, glutamic acid or iminodiacetic acid. However, it is also possible to use the sodium or potassium salts of other natural α-amino acids, of oligopeptides or of aromatic or cycloaliphatic amino carboxylic acids, eg. anthranilic acid, phenylglycine, phenylalanine or 1-aminocyclohexane-1-carboxylic acid. Amino carboxylic acids in this connection are particularly compounds with a primary or secondary amino group and one or two carboxyl groups per molecule; however, it is also possible in principle to use compounds with more than one amino group and/or more than two carboxyl groups, in which case the amount of alkyl carboxylates depends on the number of amino groups. All the carboxyl groups are present virtually completely in the salt form.

The process according to the invention can likewise be applied particularly satisfactorily when the technical alkali metal salts of amino sulfonic acids are the sodium or potassium salts of aliphatic amino sulfonic acids having 2 to 10 carbons, preferably 2 to 4 carbons. of particular interest in this connection are the corresponding salts of taurine (2-aminoethanesulfonic acid) and N-methyltaurine. Just like the amino carboxylic acids, it is possible for the amino sulfonic acids used, which are likewise present virtually completely in the alkali metal salt form, to have a plurality of amino groups and/or sulfonic acid groups.

Besides the sodium or potassium salts, it is likewise possible to use the corresponding lithium salts.

Particularly suitable alkyl carboxylates are lower alkyl esters of fatty acids, ie. $C_1$–$C_4$-alkyl esters of saturated or unsaturated $C_6$–$C_{30}$-monocarboxylic acids. Particularly suitable are the methyl esters of saturated or unsaturated $C_8$–$C_{20}$-monocarboxylic acids, eg. methyl laurate, methyl myristate, methyl palmitate, methyl stearate, methyl oleate, methyl linoleate or methyl linolenate or mixtures of such esters of naturally occurring long chain fatty acids, eg. coconut fatty acid methyl ester, palm oil fatty acid methyl ester, palm kernel oil fatty acid methyl ester, tallow fatty acid methyl ester, soybean oil fatty acid methyl ester, sunflower oil fatty acid methyl ester or rape seed oil fatty acid methyl ester, and corresponding esters of synthetic $C_8$–$C_{20}$-monocarboxylic acids or mixtures thereof. The process according to the invention can be carried out both in a batchwise and in a continuous procedure.

The process according to the invention can be used to prepare pure N-acylamino carboxylic acids and N-acylamino sulfonic acids and their alkali metal salts or mixtures of such compounds with different acyl radicals and/or different basic amino carboxylic acids or amino sulfonic acids. Compounds of this type are known to be suitable as emulsifiers or surfactants in a wide variety of industrial sectors.

The process according to the invention provides good space-time yields of the desired products of high purity. The relatively mild temperature conditions mean that no decomposition reactions leading to reductions of yield and darkening of color of the products occur. The reactions have gone to completion in a considerably shorter time.

The use of alkyl carboxylates as acylating components of reasonable cost and ease of handling, and the avoidance of salt formation in the acylation make the process according to the invention, especially in a continuous procedure, extremely attractive for the industrial scale.

A noteworthy point about the present process according to the invention is that by increasing the content of strong bases in the reaction mixture beyond the normal catalytic amounts, the loss of selectivity of the reaction on use of technical, ie. impure, alkali metal amino carboxylates or sulfonates in place of the pure salts is substantially compensated. This is all the more surprising since there is a prejudice in the literature that aliphatic carboxylic esters do not react with secondary amines in the presence of equimolar amounts of base such as sodium methanolate to give the corresponding amides (R. J. de Feoand and P. D. Strickler, J. Org. Chem. 28 (1963) 2915–2917). Example 2 hereinafter, with sarcosine sodium, a secondary amine, clearly contradicts this prejudice.

EXAMPLES

Example 1 (for comparison)
Preparation of N-oleoylsarcosine using conventional catalytic amounts of sodium methanolate 1 mole of methyl oleate (Edenor® ME TiO5 from Henkel) and 1 mole of anhydrous technical sarcosine sodium powder (active content: 84.4% by weight sarcosine sodium) were placed in a beaker and mixed using an Ultra-Turrax to give a fine suspension. The suspension was transferred into a glass reactor and heated to 120° C. Under a nitrogen atmosphere, 25 mol % of sodium methanolate as an approximately 30% by weight solution in methanol were metered in with stirring over the course of 10 minutes. After the addition was complete, the mixture was stirred at 120° C. until carboxylate was no longer detectable in the IR spectrum (about 3.5 hours). The reaction mixture was then cooled to 100° C. and 600 ml of water were added. The mixture was stirred until a clear aqueous solution was produced.

100 g of 96% by weight sulfuric acid were added to this solution. A creamy emulsion formed, and this separated into a two-phase mixture after addition of 80 g of methyl ethyl ketone. This mixture was separated in a separating funnel, and the aqueous phase was discarded. The methyl ethyl ketone was distilled out of the organic phase at <50° C. and about 40 mbar and was reused. The residue was an orange-brown oil with a content, determined by HPLC, of 76.7% by weight N-acylsarcosine; the yield was 290 g (corresponding to 83.5% of theory).

Example 2 (according to the invention)
Preparation of N-oleoylsarcosine using equimolar amounts of sodium methanolate The experiment described in Example 1 was repeated with the difference that 100 mol % were used in place of 25 mol % sodium methanolate. Working up resulted in an orange-brown oil with a content, determined by HPLC, of 82.9% by weight N-acylsarcosine; the yield was 322 g (corresponding to 92.5% of theory).

Example 3 (according to the invention)
Preparation of N-oleoylsarcosine using above-stoichiometric amounts of sodium methanolate The experiment described in Example 1 was repeated with the difference that 110 mol % were used in place of 25 mol % sodium methanolate. Working up resulted in an orange-brown oil with a content, determined by HPLC, of 85.2% by weight N-acylsarcosine; the yield was 320 g (corresponding to 91.9% of theory).

We claim:

1. A process for preparing N-acylamino carboxylic acids and N-acylamino sulfonic acids and their alkali metal salts from the technical alkali metal salts of amino carboxylic acids and amino sulfonic acids, respectively, with an active content of 50–95% by weight, based on the solids content of the technical alkali metal salts, and from alkyl carboxylates, which comprises
    (a) preparing a suspension of the solid anhydrous technical alkali metal salts of the amino carboxylic acids or amino sulfonic acids in the alkyl carboxylates,
    (b) reacting this suspension by adding 30 to 150 mol % of strong bases over the amount required for neutralization to give the alkali metal salts of the N-acylamino carboxylic acids or N-acylamino sulfonic acids, and
    (c) if required preparing therefrom the free N-acylamino carboxylic acids or N-acylamino sulfonic acids in a conventional way by adding acids.

2. A process as claimed in claim 1, wherein in step (a) a suspension of equimolar or approximately equimolar amounts of technical alkali metal salts of amino carboxylic acids or amino sulfonic acids and alkyl carboxylates is prepared.

3. A process as claimed in claim 1, wherein in step (b) the strong bases are used in amounts of from 70 to 120 mol %, based on the technical alkali metal salts of the amino carboxylic acids or amino sulfonic acids.

4. A process as claimed in claim 1, wherein in step (b) alkali metal alcoholates are used as strong bases.

5. A process as claimed in claim 1, wherein the reaction in step (b) is carried out at from 50° to 150° C.

6. A process as claimed in claim 1, wherein the sodium or potassium salts of aliphatic amino carboxylic acids having 2 to 10 carbons are used as technical alkali metal salts of amino carboxylic acids.

7. A process as claimed in claim 1, wherein the sodium or potassium salts of aliphatic amino sulfonic acids having 2 to 10 carbons are used as technical alkali metal salts of amino sulfonic acids.

8. A process as claimed in claim 1, wherein the $C_1$–$C_4$-alkyl esters of saturated or unsaturated $C_6$–$C_{30}$-monocarboxylic acids are used as alkyl carboxylates.

* * * * *